(12) United States Patent
Walter et al.

(10) Patent No.: US 11,631,479 B2
(45) Date of Patent: Apr. 18, 2023

(54) PATIENT RECRUITMENT SYSTEM

(71) Applicant: Clinerion Ltd., Basel (CH)

(72) Inventors: Andreas Walter, Baden-Baden (DE); Dominik Aronsky, Rueschlikon (CH); Bernhard Bodenmann, Binningen (CH); Lukasz Strzepka, Staufen (CH); Ulf Claesson, Wettswil (CH)

(73) Assignee: Clinerion Ltd., Basel (CH)

( * ) Notice: Subject to any disclaimer, the term of this patent is extended or adjusted under 35 U.S.C. 154(b) by 526 days.

(21) Appl. No.: 16/635,701

(22) PCT Filed: Aug. 4, 2017

(86) PCT No.: PCT/EP2017/069859
§ 371 (c)(1),
(2) Date: Jan. 31, 2020

(87) PCT Pub. No.: WO2019/025015
PCT Pub. Date: Feb. 7, 2019

(65) Prior Publication Data
US 2021/0005295 A1  Jan. 7, 2021

(51) Int. Cl.
| | |
|---|---|
| G16H 10/60 | (2018.01) |
| G16H 40/20 | (2018.01) |
| G16H 50/70 | (2018.01) |
| G16H 10/20 | (2018.01) |
| G06F 16/245 | (2019.01) |
| G06F 16/25 | (2019.01) |
| G06F 21/62 | (2013.01) |

(52) U.S. Cl.
CPC ............ *G16H 10/60* (2018.01); *G06F 16/245* (2019.01); *G06F 16/258* (2019.01); *G06F 21/6254* (2013.01); *G16H 10/20* (2018.01); *G16H 40/20* (2018.01); *G16H 50/70* (2018.01)

(58) Field of Classification Search
CPC ........ G16H 10/20; G16H 10/60; G16H 40/20; G16H 50/70; G06F 21/6245; G06F 21/6254
See application file for complete search history.

(56) References Cited

U.S. PATENT DOCUMENTS

| | | | |
|---|---|---|---|
| 2003/0039362 A1 | 2/2003 | Califano et al. | |
| 2008/0010254 A1* | 1/2008 | Settimi ................. | G06Q 10/06 |
| 2011/0253139 A1 | 10/2011 | Guthrie et al. | |
| 2012/0101843 A1* | 4/2012 | Mathur ................. | G06Q 40/08 705/2 |
| 2012/0191749 A1* | 7/2012 | New ...................... | G16H 10/20 707/769 |
| 2012/0303616 A1* | 11/2012 | Abuelsaad ............ | G06F 16/122 707/736 |
| 2013/0204914 A1* | 8/2013 | Behram ................. | G16H 10/60 708/200 |
| 2013/0304542 A1* | 11/2013 | Powell ............... | G06Q 30/0201 705/7.32 |
| 2014/0316793 A1 | 10/2014 | Pruit | |
| 2015/0149208 A1* | 5/2015 | Lynch ................... | G16H 10/60 705/3 |
| 2016/0147945 A1* | 5/2016 | MacCarthy ........... | H04W 12/02 705/51 |
| 2017/0053069 A1* | 2/2017 | Walter ................... | G16H 10/60 |
| 2017/0076046 A1 | 3/2017 | Barnes et al. | |

FOREIGN PATENT DOCUMENTS

| | | | | |
|---|---|---|---|---|
| WO | 2009/065043 A1 | 5/2009 | | |
| WO | WO-2010135578 A2 * | 11/2010 | ........... | G06F 19/322 |
| WO | 2010/149948 A2 | 12/2010 | | |
| WO | 2017/042396 A1 | 3/2017 | | |

OTHER PUBLICATIONS

International Search Report dated Apr. 24, 2018 issued in corresponding International Patent Application No. PCT/EP2017/069859.
International Preliminary Report on Patentability dated Feb. 4, 2020 issued in corresponding International Patent Application No. PCT/EP2017/069859.
Office Action dated Nov. 25, 2020 issued in corresponding EP Patent Application No. 17749184.2. (and English machine translation).

* cited by examiner

*Primary Examiner* — Robert W Morgan
*Assistant Examiner* — Chance L Smith
(74) *Attorney, Agent, or Firm* — Posz Law Group, PLC

(57) ABSTRACT

A patient recruitment system, in particular for clinical studies, has at least one database environment comprising at least one database module that is configured at least to store in a patient database at least patient data records containing at least one course of treatment of at least one patient, has at least one patient recruitment server comprising at least one patient recruitment module that is configured to search and at least compare with at least one recruitment feature, data records, in particular courses of treatment, and has a data transport unit for a data transfer, in particular of at least one course of treatment, between the database environment and the patient recruitment server, the data transport unit comprises a restriction module, which restricts the data transfer to outbound connections originating from the database environment.

7 Claims, 3 Drawing Sheets

PATIENT RECRUITMENT SYSTEM

CROSS REFERENCE TO RELATED APPLICATION

This application is a U.S. national stage application of PCT/EP2017/069859 filed on Aug. 4, 2017, the contents of which are incorporated herein by reference.

PRIOR ART

The invention relates to a patient recruitment system according to the preamble of claim 1, and to a method for recruiting patients according to the preamble of claim 15.

A patient recruitment system, in particular for clinical studies, has already been proposed which has at least one database environment comprising at least one database module that is configured at least to store in a patient database at least patient data records containing at least one course of treatment of at least one patient, which has at least one patient recruitment server comprising at least one patient recruitment module that is configured to search and at least compare with at least one recruitment feature, data records, in particular courses of treatment, and which has a data transport unit for a data transfer, in particular of at least one course of treatment, between the database environment and the patient recruitment server.

The object of the invention is in particular to provide a system of the type in question that has improved properties as regards data transmission, in particular in terms of data protection. The object is achieved according to the invention by the features of claims 1 and 15, while advantageous embodiments and developments of the invention can be found in the dependent claims.

Advantages of the Invention

The invention is based on a patient recruitment system, in particular for clinical studies, which has at least one database environment comprising at least one database module that is configured at least to store in a patient database at least patient data records containing at least one course of treatment of at least one patient, which has at least one patient recruitment server comprising at least one patient recruitment module that is configured to search and at least compare with at least one recruitment feature, data records, in particular courses of treatment, and which has a data transport unit for a data transfer, in particular of at least one course of treatment, between the database environment, in particular a patient recruitment module of the database environment, and the patient recruitment server, in particular a patient recruitment module of the patient recruitment server.

It is proposed that the data transport unit comprises a restriction module, which restricts the data transfer to outbound connections originating from the database environment. It is hence advantageously possible to improve a data transmission, in particular in terms of data security. This advantageously means that sensitive data, in particular patient data, can be transmitted securely. In particular, the data transport unit at the database-environment end has no inbound ports and has solely outbound ports, whereby it can be ensured advantageously that connections between the database environment and the patient recruitment server are initiated always from the database-environment end. It can hence be achieved advantageously that the data transfer conveyed by the data transport unit is completely transparent for the database-environment end. In addition, it is advantageously possible to prevent unauthorized access to the database environment by means of the data transport unit, for instance by "hacking". The patient recruitment system can be used advantageously to simplify anonymized identification of suitable subjects for a clinical study, thereby advantageously allowing internal processes in a hospital to be optimized and/or accelerated. This can advantageously reduce costs.

A "database environment" shall in particular mean a computer system, in particular a supervisory computer system. The database environment preferably comprises at least part of a hospital information system, in particular having electronically stored patient records and/or electronically stored progressions of a disease, and/or comprises at least one database module belonging to the hospital information system and having at least one patient database containing patient data records and/or patient information. The database environment is preferably embodied as a dedicated computer system or as at least part of a dedicated computer system, although alternatively could also be embodied at least partially as a virtual server, as a plurality of distributed servers or as a server in a, in particular private and/or public, Cloud. In particular, the database environment is situated inside an Intranet of the hospital information system, preferably in a specially secured and/or access-restricted sector of the Intranet of the hospital information system. The database environment is advantageously located in a, preferably access-restricted and/or specially secured, room of the hospital. The database environment also preferably comprises additional components, in particular for anonymizing patient data records by means of an anonymization module, for initiating data transport by means of a data transport unit, for initiating at least one request for data records from a server and/or a computer system outside the database environment by means of a patient recruitment module of the database environment, and/or for calculating identifiers belonging to data records by means of an identifier module. The access to the database environment and/or to at least one component, preferably all the components, of the database environment is protected, in particular password-protected. The database environment is preferably protected by means of at least one firewall and/or preferably by means of additional protective components such as, for instance, an intrusion detection system (IDS) and/or an intrusion prevention system (IPS). In the patient database can be stored in particular patient data records in unencrypted, or preferably encrypted, form. A patient data record comprises in particular at least one patient data record such as, for instance, at least one treatment carried out, e.g. an operation, at least one diagnosis, e.g. a diagnosis of an illness, a symptomatic diagnosis, and/or a specific physiological quantity such as blood pressure, lung capacity, body fat percentage, and/or suchlike, at least one medication history, e.g. a medication dose, a medication period, a drug intolerance, and/or suchlike, at least one procedure, at least laboratory data such as blood test results, for instance, and/or at least personalized data such as, for instance, age, weight, height, gender, origin, date of birth, name, health insurance information, and/or address. A patient data record preferably corresponds at least in part to an electronic patient record of a hospital. Each patient data record is preferably assigned a unique patient identifier. A "data record" shall be understood to mean in particular a patient data record or an anonymized patient data record. A "course of treatment" shall be understood to mean in particular a sequence, in particular a chronological sequence, of at least one treatment, at least one diagnosis, and/or at least one medication. In particular, the patient data record comprises a set of all known courses of treatment of a patient. The anonymized patient data record preferably comprises an anonymized set of all courses of treatment of a patient.

A "patient recruitment server" shall be understood to mean in particular a server which is configured for patient recruitment on the basis of, in particular anonymized, patient data records from at least one health care institution, for example from an out-patient medical center, a medical practice, and/or preferably from a hospital. A patient recruitment module of the database environment preferably communicates with a patient recruitment module of the patient recruitment server by means of a data transport unit deemed practical by a person skilled in the art that allows solely outbound connections originating from the database environment, preferably by means of server-to-server communication. The patient recruitment server and the database environment are preferably in a distributed arrangement, in particular in different locations. The patient recruitment server is preferably embodied as a dedicated server, although alternatively could also be embodied as a virtual server, as a plurality of distributed servers or as a server in a Cloud. The patient recruitment server is preferably located within the Intranet of the hospital information system. At least one firewall is preferably interposed between the patient recruitment server and the database environment. The patient recruitment server is preferably located behind a firewall of the hospital information system. The database environment, in particular networks of the database environment, and the patient recruitment server, in particular networks of the patient recruitment server, are designed to be logically separate from one another. Communication between the database environment and the patient recruitment server is preferably encrypted, for instance by means of an SSL and/or HTTPS protocol. The patient recruitment server is located in particular in what is known as a demilitarized zone of a hospital information system. The patient recruitment server is preferably configured to associate, in particular anonymized, patient data records on the basis of recruitment features with a procedure deemed practical by a person skilled in the art, advantageously with clinical studies and/or prognoses about progressions of a disease. The patient recruitment module of the database environment can be embodied advantageously as a separate server inside the database environment. Alternatively, the anonymization module can be integrated advantageously in a server of the database environment, for instance a database server of the database environment. A "recruitment feature" shall be understood to mean in particular a requirement that is satisfied by a subset of the patient data records. Patient data records can preferably be accepted into the subset, or excluded from the subset, by means of the recruitment feature. The recruitment feature is preferably realized as a requirement that contains at least one criterion for participation in at least one clinical study, for example at least one specific physiological property, diagnosis and/or medication. The recruitment feature can include in particular a maximum age, a minimum age, at least one diagnosis, at least one laboratory value, at least one sensor value, at least one medication dose, at least one course of medication, at least vital signs, for instance a blood pressure, and/or a weight. A recruitment feature preferably comprises a combination of a plurality of criteria.

A "data transport unit" shall be understood to mean a unit that is configured to transmit information, in particular patient data records, preferably anonymized patient data records, from a transmitter of the data transport unit to a receiver of the data transport unit. In particular, transmitter and receiver can form parts of mutually distinct computer systems and/or servers, preferably with transmitter and receiver arranged within a shared Intranet. Data transmission between transmitter and receiver preferably takes place within a solid body, for instance by means of a, in particular serial or parallel, wired connection, and/or wirelessly. In particular, the data transport unit can comprise a restriction module, which is configured to monitor a data transfer, and/or to restrict a data transfer on the basis of specific criteria such as, for instance, a dataflow direction, a data volume, a data composition, and/or a data type. The restriction module is embodied in particular as at least one firewall and/or as additional programming of the data transport unit, which programming influences data traffic. An "outbound connection" shall be understood to mean in particular a connection of the data transport unit, in particular between at least part of the database environment and the patient recruitment server, that can be initiated solely from the database-environment end. In particular, data transport between at least part of the database environment and the patient recruitment server by means of an outbound connection can be controlled solely from the database-environment end. In particular, the data transport unit has no open ports at the database environment-end. In particular, the patient recruitment server can send to the database environment solely data that has been requested previously from the database-environment end. The data transfer by means of the outbound connection, in particular between the database environment and the patient recruitment server, preferably does not include any unanonymized data records, in particular any unanonymized patient data records. The data transfer by means of the outbound connection, in particular between the database environment and the patient recruitment server, preferably does not include any identifiers and/or features from which a person and/or a patient can be uniquely identified, in particular in compliance with data protection regulations and legislation. "Configured" is in particular to mean specifically programmed, designed and/or equipped. An object being configured for a specific function shall be understood in particular to mean that the object fulfills and/or performs this specific function in at least one usage state and/or operating state.

It is also proposed that the database environment comprises an anonymization module, which is configured to convert patient data records into anonymized patient data records, in particular anonymized courses of treatment, in particular before a data transfer by means of the data transport unit to the patient recruitment server. Comprehensive data protection can advantageously be facilitated, whereby it is possible in particular to achieve a high level of security. It is hence advantageously possible to increase a willingness in particular of hospitals, patients and/or doctors to use and/or accept the patient recruitment system, as a result of which it is possible to improve, simplify and/or speed up in particular organizing clinical studies. Anonymization can advantageously improve a data transmission, in particular in terms of data security. This advantageously means that sensitive data, in particular patient data, can be transmitted securely. The anonymization module is embodied in particular as part of the database environment. The anonymization module is configured in particular to remove identifying features from patient data records, which identifying features may result in, in particular unique, identification of a patient. Identifying features include, for example, name, date of birth, place of birth, address, information about family members, social security number, and/or other identification features that can be uniquely attributed to a person, for instance features such as biometric data, unique identifiers of the patient data records, and/or identifiers of the courses of treatment within the patient database. An anonymized patient data record in particular has no identifying features. It is conceivable that the anonymization module assigns to a patient data record an anonymized static and/or time-variable identifier, although a patient data record preferably does not have any identifiers after editing by the anonymization module. In particular, a time-variable identifier may be re-assigned and/or recalculated, for example, whenever an, in particular anonymized, patient data record is edited and/or updated. The anonymization module can be embodied advantageously as a separate server inside the database environment. Alternatively, the anonymization module can be integrated advantageously in a server of the database environment, for instance a database server of the database environment. Each patient database is preferably assigned an anonymization module. The anonymization module is preferably interposed at least between the database module and the restriction module. The database module advantageously comprises an anonymized patient database, which in particular is separate from the patient database and in which is stored and/or may be stored anonymized patient data.

It is also proposed that patient data records anonymized by the anonymization module, in particular with regard to data security regulations and/or doctor-patient confidentiality, do not have any identifiers and/or identifying features that can be uniquely attributed to a patient. It is hence advantageously possible to achieve particularly complete anonymization, thereby advantageously allowing an improvement in data protection. It is hence advantageously possible to increase a willingness in particular of hospitals, patients and/or doctors to use and/or accept the patient recruitment system, as a result of which it is possible to improve, simplify and/or speed up in particular organizing clinical studies. Anonymization can advantageously improve a data transmission, in particular in terms of data security. This advantageously means that sensitive data, in particular patient data, can be transmitted securely. An identifier, in particular an identifier that can be uniquely attributed to a patient, is in particular realized as a feature linked to a specific identity, for instance to a person and/or a data record, for unique identification of the identity, for instance of the person and/or of the data record. In particular, a social security number, an identity-card number, a passport number, a health insurance number, a patient number and/or a customer number can form an identifier.

It is also proposed that the database environment comprises an identifier module, which calculates a unique anonymized identifier on the basis of an anonymized patient data record. It is hence advantageously possible to improve data organization, thereby allowing in particular an increase in efficiency. Advantageously, in particular by using solely already anonymized data to calculate the anonymized identifier, the anonymized identifier is advantageously independent of components uniquely attributable to a person and/or to an identifying feature. An anonymized identifier is in particular realized as a feature linked to a specific data record, for example a patient data record, for unique identification of the data record, in particular anonymized patient data record, while retaining anonymity of an identity, for example of a person associated with the data record, in particular anonymized patient data record. The expression that an anonymized identifier is "calculated on the basis of an anonymized patient data record" shall be understood to mean in particular that features and/or attributes of the anonymized patient data record are used to calculate the anonymized identifier. In particular, the anonymized identifier can be calculated from a unique signature of the anonymized patient data record. The unique signature in particular can include at least some of the patient data of the anonymized patient data record, for instance a hospital admittance date. The identifier module can be embodied advantageously as a separate server inside the database environment. Alternatively, the identifier module can be integrated advantageously in a server of the database environment, for instance a database server of the database environment and/or a server of the anonymization module. Each anonymized patient database of the database module is preferably assigned an identifier module. In particular, the anonymized identifiers remain permanently in the database environment, in particular until deletion, and/or cannot be sent out by the data transport unit. The restriction module of the data transport unit preferably prevents anonymized identifiers being sent out.

It is also proposed that the database environment comprises an assignment module, which assigns the anonymized identifier to a patient data record from the patient database, which patient data record is associated with the anonymized patient data record. This can advantageously facilitate reverse identification, in particular reverse identification restricted internally to the database environment, of an anonymized patient data record. The assignment module can be embodied advantageously as a separate server inside the database environment. Alternatively, the assignment module can be integrated advantageously in a server of the database environment, for instance a database server of the database environment. Each patient database of the database module and/or each identifier module is preferably assigned an assignment module. In particular, the assignment module is interposed between the patient database and the identifier module. In particular, the database module stores a table that comprises at least one associated list of anonymized identifiers and uniquely attributable identifiers and/or identifying features. The table preferably includes, in particular additionally, at least one anonymized patient data record associated with an anonymized identifier, and/or at least one patient data record associated with an anonymized patient data record.

It is also proposed that the anonymized identifier is embodied as a unique checksum calculated by the identifier module. It is hence advantageously possible to improve data organization, thereby allowing in particular an increase in efficiency. In addition, data protection can advantageously be improved, in particular by means of high immunity of a checksum to decryption and/or back calculation. A calculation of the checksum, and/or a method for calculating the checksum, is advantageously concealed from outside view, in particular cannot be seen from outside the identifier module, in particular is secret with respect to the outside. It is hence advantageously possible to increase a willingness in particular of hospitals, patients and/or doctors to use and/or accept the patient recruitment system, as a result of which it is possible to improve, simplify and/or speed up in particular organizing clinical studies. The checksum can be determined in particular by means of at least one digit sum, at least one parity check, at least one Fletcher checksum routine, at least one cyclic redundancy check, at least one modulo calculation, and/or at least one further calculation method deemed practical by a person skilled in the art. Alternatively or additionally, an implementation of the checksum can include at least one universally unique identifier (UUID) and/or at least one serialized string.

An encryption module of the database environment is also proposed, which encrypts at least the anonymized identifiers associated with at least one anonymized patient data record, and/or encrypts a table of the database module. Immunity to unauthorized access to sensitive data can advantageously be improved. It is hence advantageously possible to improve data protection, in particular by means of additional encryption of the anonymized identifiers and/or of the table at the database-environment end. It is hence advantageously possible to increase a willingness in particular of hospitals, patients and/or doctors to use and/or accept the patient recruitment system, as a result of which it is possible to improve, simplify and/or speed up in particular organizing clinical studies. The encryption module can be embodied advantageously as a separate server inside the database environment. Alternatively, the encryption module can be integrated advantageously in a server of the database environment, for instance in the assignment module of the database environment and/or a database server of the database environment. Each patient database and/or each table of the database module is preferably assigned an encryption module. In particular, the encryption module is interposed between the identifier module and the assignment module. The encryption module preferably encrypts the anonymized identifiers and/or the table at least by means of a symmetric encryption method, in particular sufficient to the prior art, for instance a symmetric encryption method such as AES, IDEA, Blowfish, or by means of an RSA method.

It is also proposed that the identifier module uses for calculating the anonymized identifier at least one time, in particular a hospital admittance date, and/or at least one medical diagnosis, in particular associated with the time, preferably with the hospital admittance date, at least one dosage, in particular of a medication, which dosage in particular is associated with the time, preferably with the hospital admittance date, at least one laboratory value, in particular associated with the time, preferably with the hospital admittance date, and/or at least one medication, in particular a course of medication, in particular associated with the time, preferably with the hospital admittance date. This can advantageously make it possible to calculate a unique anonymized identifier. In addition, an identifier, in particular a time-variable anonymized identifier, which in particular is different after each update of a patient data record, can advantageously be made possible. It is conceivable that the identifier module uses at least one text and/or at least one numerical value in the anonymized patient data record to calculate the anonymized identifier. The time may include, in particular, a hospital admittance date, a hospital discharge date, a diagnosis date, a treatment date, and/or a date of administering and/or prescribing a medication.

It is also proposed that when an anonymized patient data record is updated that already exists in an anonymized patient database of the database module and is already provided, in particular by the assignment module, with an anonymized identifier, in particular when the associated course of treatment is updated, the identifier module assigns to the associated anonymized patient data record a unique updated, anonymized identifier, which has been calculated on the basis of an associated updated, anonymized patient data record, and which differs from the anonymized identifier. A time-variable identifier can hence advantageously be assigned to a patient data record. This can advantageously make an unauthorized reverse identification more difficult, thereby allowing in particular an improvement in data protection. In particular, one anonymized identifier, or two or more than two anonymized identifiers, can be assigned to a patient data record in the table. In particular, at least one updated, anonymized identifier and an original, anonymized identifier, which was assigned to the patient data record before an update, can be assigned to a uniquely attributable identifier and/or identifying feature. It is also conceivable that the assignment unit assigns to the updated, anonymized identifier at least one updated, anonymized patient data record and at least one original, anonymized patient data record, which in particular corresponds to the anonymized patient data record before the update. An original assignment prior to the update can thereby advantageously remain traceable. Alternatively, in the event of an update, the assignment module overwrites the original, anonymized identifier with the updated, anonymized identifier. This can advantageously improve data protection.

It is also proposed that in a transmission of an updated, anonymized patient data record from the database environment to the patient recruitment server, the data transport unit transmits as well an original, anonymized patient data record, which in particular corresponds to the anonymized patient data record before an update.

This advantageously allows an anonymized patient data record to be updated on the patient recruitment server, whereby it is advantageously possible to prevent double or multiple entries of anonymized patient data records at a patient-recruitment-server end, in particular in a patient recruitment database of the patient recruitment server. The data transport unit preferably transmits the updated, anonymized patient data record and the original, anonymized patient data record in a form that indicates to the patient recruitment server that they belong together, for instance in at least one shared data packet and/or a shared batch of data packets. In particular, the transmission and/or update of anonymized patient data records does not involve any identifiers. It is conceivable that the patient recruitment server comprises an identifier module, which is configured to assign, in particular on the basis of a checksum, an, in particular anonymized, identifier to an anonymized patient data record received from the data transport unit. The identifier, in particular the checksum and/or a checksum calculation method of the identifier module of the patient recruitment server, is preferably different from the checksum and/or the checksum calculation method of the identifier module of the database environment. In particular, a checksum calculation within the database environment and a checksum calculation within the patient recruitment server are independent of one another. By assigning an identifier at the patient-recruitment-server end, it is advantageously possible to improve organization, and/or to speed up finding in particular at least one match of identical anonymized patient data records.

It is also proposed that the patient recruitment server comprises a data-record comparison module, which is configured to compare received anonymized patient data records with anonymized patient data records in a patient recruitment database of the patient recruitment server, and in the event of a match of at least one anonymized patient data record, to overwrite an associated database entry in the patient recruitment database with an associated updated, anonymized patient data record. This advantageously allows an anonymized patient data record to be updated efficiently on the patient recruitment server, whereby it is advantageously possible to prevent double or multiple entries of anonymized patient data records at a patient-recruitmentserver end, in particular in the patient recruitment database of the patient recruitment server. Anonymized patient data records are advantageously updated at the patient-recruitment-server end independently of any identifiers that are calculated and/or allocated in particular at the database-environment end. This can advantageously improve data protection. In particular, on receipt of an anonymized patient data record that already exists, the data-record comparison module of the patient recruitment server detects a match of the anonymized patient data records, and causes the existing anonymized patient data record to be overwritten by the jointly received updated, anonymized patient data record in the patient recruitment database. The data-record comparison module can be embodied advantageously as a separate server that is in communication with the patient recruitment server within a shared Intranet. Alternatively, the data-record comparison module advantageously may be integrated in the patient recruitment server. The data-record comparison module is preferably interposed between the receiver of the data transport unit and the patient recruitment database of the patient recruitment server. The patient recruitment database is in particular configured to store anonymized patient data records received from the data transport unit, and to release and/or keep available said data records for the patient recruitment module of the database environment to hunt through. A database entry in the patient recruitment database includes at least one updated, anonymized patient data record and/or at least one anonymized identifier in particular calculated by the identifier module of the patient recruitment server.

It is also proposed that the patient recruitment server comprises at least one Internet port, in particular to a central Cloud instance of an operator of a patient recruitment server, at least for receiving at least one recruitment feature, wherein a connection of the Internet port to the central Cloud instance is preferably embodied as an outbound connection originating from the patient recruitment server. It is hence advantageously possible to improve and/or speed up finding suitable subjects for a clinical study. Recruitment features for a large number of widely differing studies can advantageously be loaded onto the patient recruitment server. For instance, it is conceivable that by means of the Internet port, an operator of a patient recruitment server can hunt through a database for recruitment features and/or clinical studies, and can select studies of interest to him. Alternatively or additionally, it is conceivable that an organizer of clinical studies can send recruitment features to at least one patient recruitment server. It is conceivable in particular that a number of anonymized patient data records, in particular subjects, determined by the patient recruitment server on the basis of conveyed recruitment features, can be displayed to the organizer of clinical studies by means of the Internet port. The Internet port may in particular be configured to form a connection to a Cloud and/or to a, in particular virtual, server, which Cloud and/or server preferably communicates with a plurality of patient recruitment servers at different locations and can preferably be addressed from the Internet. The patient recruitment server in particular comprises a restriction module, which prevents a data transfer of anonymized patient data records to the Internet port. The patient recruitment server preferably communicates with the Internet port solely by means of an outbound connection originating from the patient recruitment server.

It is also proposed that a patient recruitment module of the database environment requests from the patient recruitment server by means of the outbound connection of the data transport unit at least one anonymized patient data record, which has been assigned at least one recruitment feature, in particular at least one combination of recruitment features, by the patient recruitment module of the patient recruitment server, and/or requests at least one recruitment feature, in particular at least one combination of recruitment features, from the patient recruitment server. This advantageously allows achieving a secure data transmission back to the database environment, in particular of a selection of suitable candidates found at the patient-recruitment-server end, thereby allowing in particular an improvement in data security. It is hence advantageously possible to transmit back to the database-environment end, independently of identifiers, suitable candidates found at the patient-recruitment-server end, in particular with the aim of reverse identification at the, in particular specially protected, database-environment end. This can advantageously allow particularly secure reverse identification in terms of data protection. Anonymized patient data records and/or recruitment features are advantageously requested by the patient recruitment module of the database environment automatically and/or at regular intervals. A "suitable candidate" shall be understood to mean in particular an anonymized patient data record with which the patient recruitment module of the patient recruitment server was able to associate successfully a recruitment feature, in particular a recruitment feature suitable for a clinical study. The patient recruitment module of the database environment in particular requests in addition to at least one suitable candidate at least one associated clinical study, whereby it can advantageously be made possible to assign the suitable candidate to a clinical study at the database-environment end. Alternatively or additionally, the patient recruitment module of the database environment requests at least one recruitment feature, in particular associated with a clinical study, whereupon the data transport unit performs a, in particular joint, return transmission of the at least one recruitment feature of the clinical study together with all the anonymized patient data records with which it was possible to associate the at least one recruitment feature, from the patient recruitment server to the database environment. In particular, the data transport unit is configured to transmit, as a result of a request for at least one anonymized patient data record, with which the patient recruitment module of the patient recruitment server has associated, in particular successfully, at least one recruitment feature, in particular a recruitment feature belonging to at least one clinical study, at least the associated anonymized patient data record. The data transport unit preferably transmits an anonymized patient data record associated with at least one recruitment feature together with the at least one recruitment feature, in particular in a data packet and/or a shared batch of data packets. The patient recruitment module of the patient recruitment server can be embodied advantageously as a separate server that is designed to communicate with the patient recruitment server, preferably within a shared Intranet. Alternatively, the patient recruitment module of the patient recruitment server advantageously may be integrated in the patient recruitment server. Data being "requested by means of an outbound connection" shall mean in particular that prior to a transmission of the data, a receive end attaches at least one requirement to the send request to the transmitter end, which send request contains data to be sent out, whereupon said transmitter end sends out and/or can send out solely data that complies with and/or fulfills the requirements.

It is also proposed that, on receipt of an anonymized patient data record requested by the patient recruitment module of the database environment, a reverse identification module of the database environment performs a reverse identification of the anonymized patient data record, in particular by recalculating and comparing at least one anonymized identifier. This can advantageously increase data security, in particular because reverse identification can take place solely in the specially secured database environment. Data protection can advantageously be improved. It is hence advantageously possible to increase a willingness in particular of hospitals, patients and/or doctors to use and/or accept the patient recruitment system, as a result of which it is possible to improve, simplify and/or speed up in particular organizing clinical studies. For the purpose of reverse identification of a received anonymized patient data record, the reverse identification module calculates an anonymized identifier on the basis of the received anonymized patient data record. The assignment module then compares the calculated anonymized identifier of the received anonymized patient data record with anonymized identifiers contained in the table of the database module. In the event of a match of an anonymized identifier in the table of the database module with a calculated anonymized identifier of the received anonymized patient data record, the assignment module identifies the associated patient data record, preferably the associated identifier of the patient data record in the patient database, that in particular contains at least one identifying feature that is uniquely attributable to a person. It is conceivable that the assignment module forwards the patient data record, preferably the patient identifier, to a display module of the database environment. The display module is configured to output at least a portion of the patient data record visually to an authorized operator, for instance by means of a screen and/or a printout. Preferably at least access to the display module and/or access to a room in which the display module is located is access-restricted and/or password-protected.

It is conceivable in particular that the database module, the patient recruitment module of the database environment, the restriction module of the data transport unit, the anonymization module, the identifier module, the assignment module, the encryption module, the reverse identification module, and/or the display module are at least partially part of a shared computer system and/or at least partially part of a shared server.

Also proposed is a method for recruiting patients, in particular for clinical studies, by means of a patient recruitment system which has at least one database environment comprising at least one database module that is configured to store in a patient database at least patient data records containing at least one course of treatment of at least one patient, which has at least one patient recruitment server comprising at least one patient recruitment module that is configured to search and at least compare with at least one recruitment feature, courses of treatment, and which has a data transport unit for a data transfer, in particular of at least one course of treatment, between the database environment and the patient recruitment server, wherein the data transfer is restricted, by a restriction module of the data transport unit, to outbound connections originating from the database environment. It is hence advantageously possible to improve a data transmission, in particular in terms of data security. This advantageously means that sensitive data, in particular patient data, can be transmitted securely. In particular, the data transport unit at the database-environment end has no inbound ports and has solely outbound ports, whereby it can be ensured advantageously that connections between the database environment and the patient recruitment server are initiated always from the database-environment end. It can hence be achieved advantageously that the data transfer conveyed by the data transport unit is completely transparent for the database-environment end. In addition, it is advantageously possible to prevent unauthorized access to the database environment by means of the data transport unit, for instance by "hacking".

The patient recruitment system according to the invention and/or the method according to the invention are not configured to be restricted to the usage and embodiment described above. In particular, the patient recruitment system according to the invention and/or the method according to the invention can comprise, in order to fulfill a functionality described herein, individual elements, components and units that differ in number from the number thereof stated herein.

DRAWINGS

The following description of the drawings reveals further advantages. An exemplary embodiment of the invention is presented in the drawings. The drawings, the description and the claims contain numerous features in combination. A person skilled in the art will expediently consider the features separately as well, and combine them into further practical combinations.

DESCRIPTION OF THE EXEMPLARY EMBODIMENTS

Figure 1:
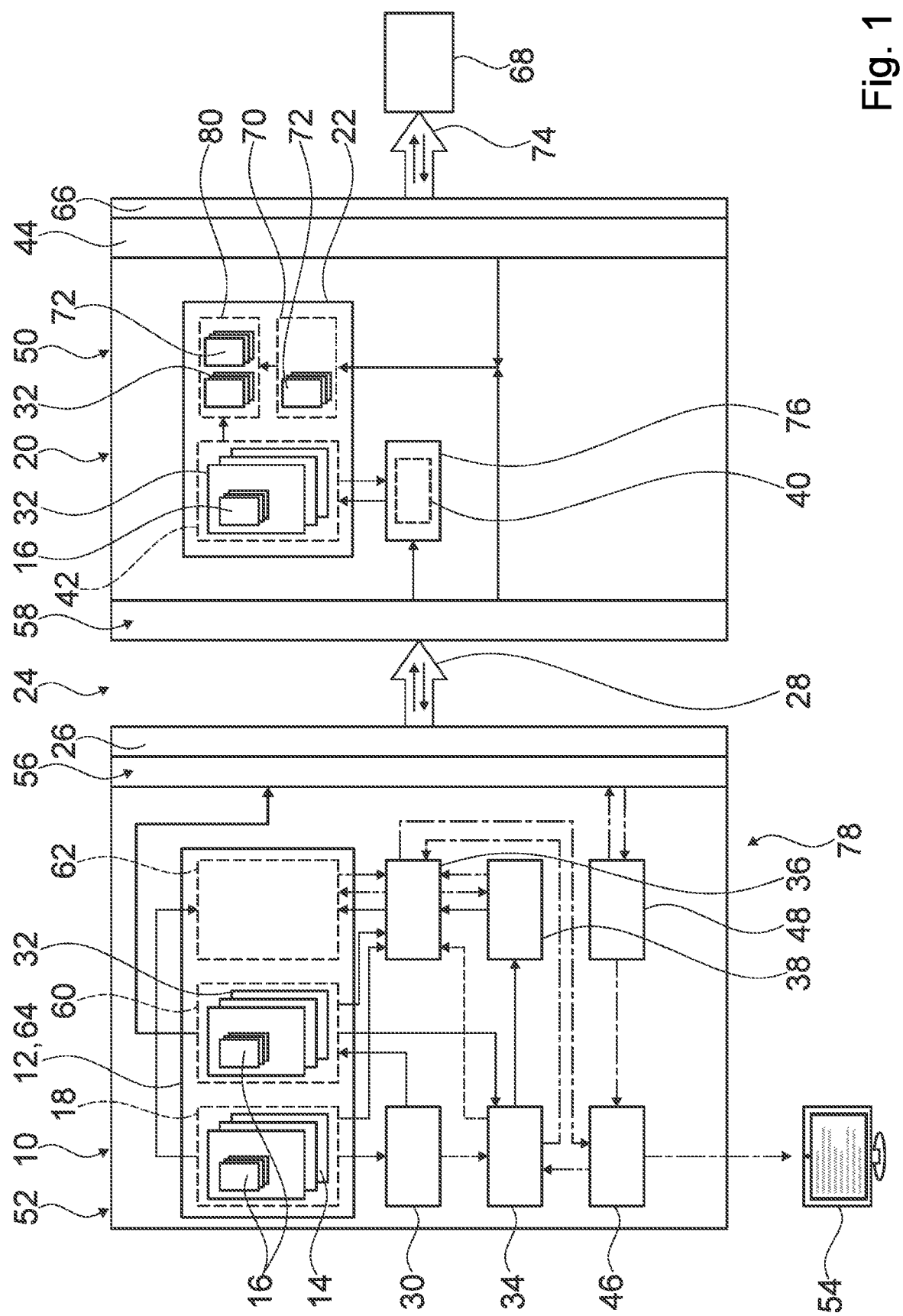
FIG. 1 is a schematic view of a patient recruitment system.

FIG. 1 shows a patient recruitment system. The patient recruitment system is configured to recruit patients for clinical studies. The patient recruitment system comprises a database environment 10. The database environment 10 comprises a database module 12. The database module is preferably embodied as a database server 64. The database module 12 is configured to store data and/or data records, in particular in databases and/or tables. The database module 12 comprises a patient database 18. Patient data records 14 can be stored in the patient database 18. A patient data record 14 comprises at least one course of treatment 16 of a patient. The database module 12 comprises an anonymized patient database 60. Anonymized patient data records 32 can be stored in the anonymized patient database 60. An anonymized patient data record 32 comprises at least one course of treatment 16 of an anonymized patient. The database module 12 comprises a table 62. Patient data records 14 can be stored in the table 62. Anonymized patient data records 32 can be stored in the table 62. Identifiers can be stored in the table 62. Anonymized identifiers can be stored in the table 62.

The patient recruitment system comprises a data transport unit 24. The data transport unit 24 is configured for a data transfer of an anonymized patient data record 32. The data transport unit 24 comprises a transmitter 56. The transmitter 56 is arranged at a database-environment end 52 of the patient recruitment system. The data transport unit 24 comprises a receiver 58. The receiver 58 is arranged at a patient-recruitment-server end 50 of the patient recruitment system. The data transport unit 24 controls a data transfer between the database environment 10 and the patient recruitment server 20. The data transport unit 24 conveys data between the database environment 10 and the patient recruitment server 20. The data transport unit 24 allows data transport from the database environment 10 to the patient recruitment server 20. The data transport unit 24 allows data transport from the patient recruitment server 20 to the database environment 10. The data transport unit 24 comprises a restriction module 26. The restriction module 26 restricts the data transfer to outbound connections 28 originating from the database environment 10. The outbound connection 28 allows data transport initiated solely by the database environment 10. The transmitter 56 controls the data transport of incoming and outgoing data.

The database environment 10 comprises an anonymization module 30. The anonymization module 30 is configured to convert patient data records 14 into anonymized patient data records 32. The anonymization module 30 receives patient data records 14 from the patient database 18. The anonymization module 30 removes identifying features from the patient data records 14. Patient data records 32 anonymized by the anonymization module 30 do not have any identifiers and/or identifying features that can be uniquely attributed to a patient. The anonymization module 30 transfers anonymized patient data records 32 to the anonymized patient database 60.

The database environment 10 comprises an identifier module 34. The identifier module 34 receives anonymized patient data records 32 from the anonymized patient database 60 and/or from a reverse identification module 46 of the database environment 10. Alternatively, it is conceivable that the anonymization module 30 forwards the anonymized patient data records 32 directly to the identifier module 34. The identifier module 34 calculates on the basis of an anonymized patient data record 32 a unique anonymized identifier. The identifier module 34 uses for calculating the anonymized identifier at least one time, at least one medical diagnosis, at least one dosage, at least one laboratory value, and/or at least one medication. The anonymized identifier is embodied as a unique checksum. The identifier module 34 calculates the checksum. The anonymized identifier is designed to vary over time; the anonymized identifier changes when an anonymized patient data record 32 changes. The identifier module 34 transfers the anonymized identifier and the associated anonymized patient data record 32 to an encryption module 38 of the database environment 10.

When an anonymized patient data record 32 is updated that already exists in the anonymized patient database 60 and is already provided with an anonymized identifier, the identifier module 34 assigns to the associated anonymized patient data record 32 a unique updated, anonymized identifier. The identifier module 34 calculates the updated, anonymized identifier on the basis of the associated updated, anonymized patient data record 32. The updated, anonymized identifier differs from the anonymized identifier. In a transmission of an updated, anonymized patient data record 32 from the database environment 10 to the patient recruitment server 20, the data transport unit 24 jointly transmits an original, anonymized patient data record 32.

The database environment 10 comprises the encryption module 38. The encryption module 38 encrypts the anonymized identifiers associated with at least one anonymized patient data record 32. The encryption module 38 receives anonymized identifiers from the identifier module 34. In addition, the encryption module 38 can be configured to decrypt anonymized identifiers. Alternatively, it is conceivable that the patient recruitment system does not have an encryption module 38, and the identifier module 34 transfers the anonymized identifiers directly to an assignment module 36 of the database environment 10 (see dashed path in FIG. 1).

The database environment 10 comprises the assignment module 36. The assignment module 36 receives encrypted or unencrypted anonymized identifiers from the encryption module 38 or from the identifier module 34. The assignment module 36 receives patient data records 14 from the patient database 18. The assignment module 36 receives anonymized patient data records 32 from the anonymized patient database 60. The assignment module 36 assigns the anonymized identifier to a patient data record 14 from the patient database 18, which patient data record is associated with the anonymized patient data record 32. The assignment module 36 stores in the table 62 an assignment of patient data records 14, anonymized patient data records 32, and anonymized identifiers. Alternatively, it is conceivable that the assignment module 36 stores in the table 62 only an assignment of patient data records 14 and anonymized identifiers.

The patient recruitment system comprises a patient recruitment server 20. The patient recruitment server 20 comprises a patient recruitment module 22. The patient recruitment module 22 comprises a recruitment feature database 70.

Recruitment features 72 can be stored in the recruitment feature database 70. The patient recruitment module 22 is configured to search data records, in particular courses of treatment 16. The patient recruitment module 22 is configured to compare anonymized patient data records 32 with at least one recruitment feature 72. The patient recruitment module 22 comprises a candidate list 80. Anonymized patient data records 32 associated with recruitment features 72 can be stored in the candidate list 80. Recruitment features 72 can be stored in the candidate list 80 such that they are associated with anonymized patient data records 32.

The patient recruitment server 20 comprises a data receiving module 76. The data receiving module 76 is configured to receive anonymized patient data records 32 from the data transport unit 24. The patient recruitment module 22 comprises a patient recruitment database 42. Anonymized patient data records 32 can be stored in the patient recruitment database 42. The data receiving module 76 is configured to store received anonymized patient data records 32 in the patient recruitment database 42. The patient recruitment server 20 comprises a data-record comparison module 40. The data-record comparison module 40 is configured to compare received anonymized patient data records 32 with anonymized patient data records 32 in the patient recruitment database 42. The data-record comparison module 40 is configured to overwrite, in the event of a match of an anonymized patient data record 32, an associated database entry in the patient recruitment database 42 with an associated updated, anonymized patient data record 32.

The patient recruitment server 20 comprises an Internet port 44. The Internet port comprises a restriction module 66. The restriction module 66 is embodied as a firewall. The Internet port 44 is used to receive at least one recruitment feature 72. The Internet port 44 is configured to establish an electronic connection to a Cloud 68. The Internet port 44 is preferably restricted to the electronic connection to the Cloud 68. The Cloud 68 is realized as a central Cloud, in particular of an operator of the patient recruitment system. The restriction module 66 restricts the communication between the patient recruitment server 20 and the Cloud to an outbound connection of the patient recruitment server 20. The Internet port 44 communicates with the Cloud 68 via the outbound connection 74 of the patient recruitment server 20. The outbound connection 74 of the patient recruitment server 20 exists between the patient recruitment server 20 and the Cloud 68. The outbound connection 74 of the patient recruitment server 20 originates solely from the patient recruitment server 20.

The database environment 10 comprises a reverse identification unit 78. The reverse identification unit 78 is formed partially integrally with the database environment 10. A unit and an environment being formed "partially integrally" shall be understood to mean in particular that the unit and the environment comprise at least one, in particular at least two, advantageously at least three, elements in common, which are a constituent part, in particular a functionally important constituent part, of both units. In FIG. 1, dotted-dashed lines are used to identify a communication path of the reverse identification unit 78 in the event of reverse identification of an anonymized patient data record 32, with which at least one recruitment feature 72 has been associated at the patient-recruitment-server end 50.

The database environment 10 comprises a patient recruitment module 48. The patient recruitment module 48 of the database environment 10 is configured at least to request from the patient recruitment server 20 an anonymized patient data record 32 with which a recruitment feature 72 is associated. The patient recruitment module 48 of the database environment 10 requests by means of the outbound connection 28 an anonymized patient data record 32 with which a recruitment feature 72 is associated. The database environment 10 comprises a reverse identification module 46. The reverse identification module 46 is configured to receive from the patient recruitment module 48 of the database environment 10 anonymized patient data records 32 with which a recruitment feature 72 is associated. On receipt of an anonymized patient data record 32, the reverse identification module 46 performs a reverse identification of the anonymized patient data record 32. The aim of the reverse identification is to associate an anonymized patient data record 32 with a patient data record 14. The database environment 10 comprises a display module 54. The display module 54 is configured for visual display at least of patient data records 14 reverse-identified by the reverse identification module 46.

Figure 2:
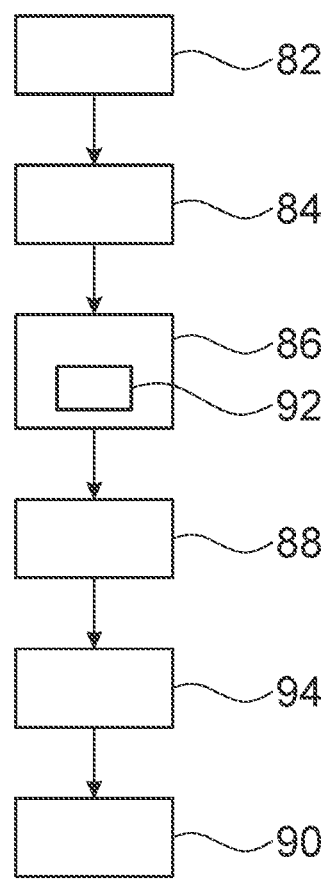
FIG. 2 is a flow diagram for a method for recruiting patients.

In the method shown in FIG. 2 for recruiting patients, in at least one method step 82, the anonymization module 30 anonymizes patient data records 14. In at least one further method step 84, the anonymized patient data records 32 are stored in the anonymized patient database 60. In at least one further method step 86, the anonymized patient data records 32 are sent out by the data transport unit 24. In at least one further method step 92, the restriction module 26 restricts the data transfer to outbound connections 28 originating from the database environment 10. In at least one further method step 88, the data receiving module 76 of the patient recruitment server 20 receives the anonymized patient data records 32. In at least one further method step 94, the patient recruitment module 22 performs patient recruitment by searching the anonymized patient data records 32 with regard to at least one recruitment feature 72. In at least one further method step 90, the reverse identification unit 78 performs a reverse identification of suitable candidates found in the patient recruitment.

Figure 3:
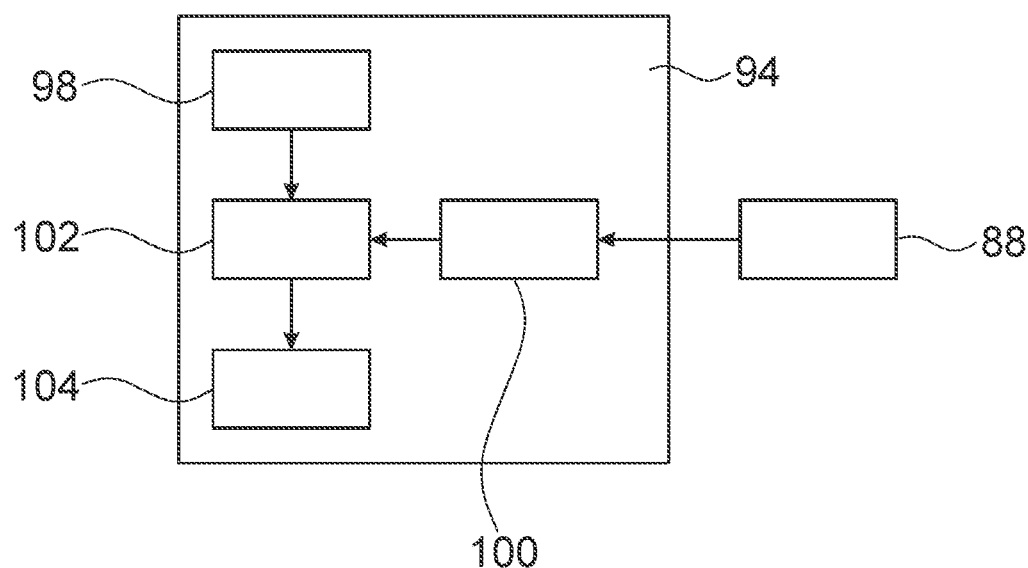
FIG. 3 is a flow diagram of part of the method.

FIG. 3 shows a flow diagram of method steps that proceed at least partially within the method step 94. In at least one method step 98, the patient recruitment module 22 receives recruitment features 72 by means of the Internet port 44, and stores said recruitment features in the recruitment feature database 70. In at least one further method step 100, the data-record comparison module 40 replaces anonymized patient data records 32 already held in the patient recruitment database 42 with newly received updated, anonymized patient data records 32. In at least one further method step 102, the anonymized patient data records 32 of the patient recruitment database 42 are searched for matches with at least one recruitment feature 72 by the patient recruitment module 22. In at least one further method step 104, anonymized patient data records 32, which could be associated to at least one recruitment feature 72, are stored in the candidate list 80.

Figure 4:
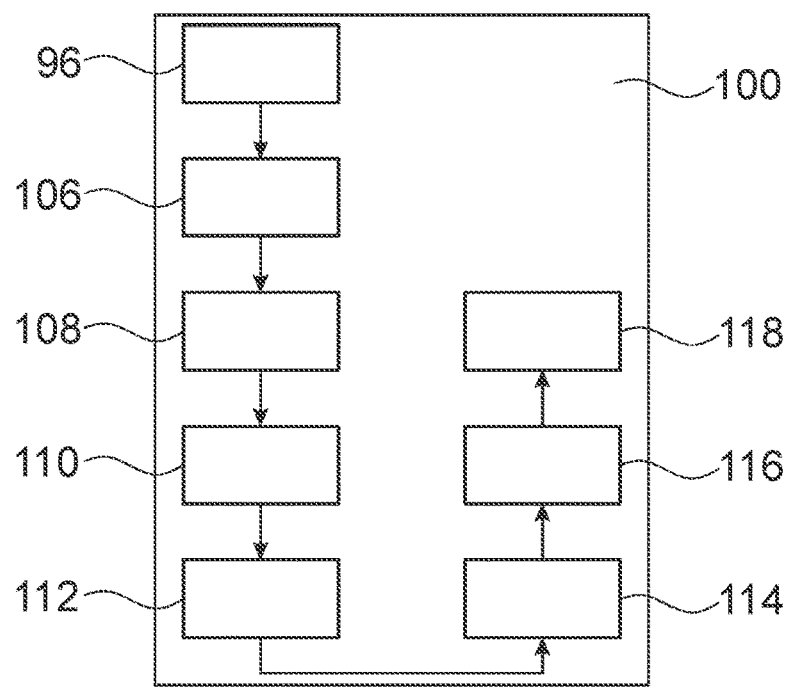
FIG. 4 is a flow diagram of a further part of the method.
Figure 5:
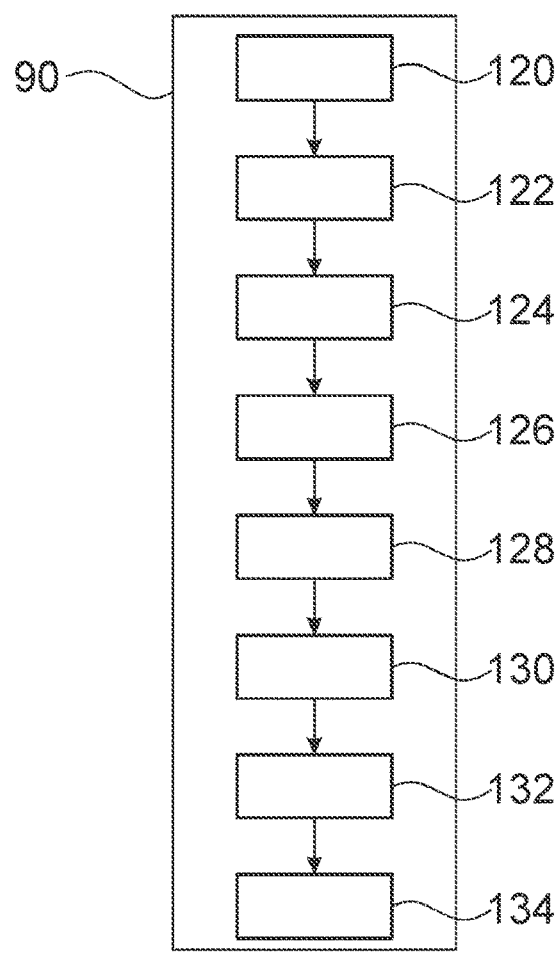
FIG. 5 is a flow diagram of an additional further part of the method.

FIG. 4 shows a flow diagram of method steps proceeding at least partially within the method step 100. In at least one method step 96, a patient data record 14 is updated in the patient database 18, for instance with a diagnosis that has been newly added to a course of treatment 16. In at least one further method step 106, the updated patient data record 14 is stored in the patient database 18 and the patient data record 14 is thereby overwritten. In at least one further method step 108, the updated patient data record 14 is anonymized by the anonymization module 30. In at least one further method step 110, the updated, anonymized patient data record 32 is stored in the anonymized patient database 60 together with the previous anonymized patient data record 32 belonging to the same patient. In at least one further method step 112, the data transport unit 24 transmits to the patient recruitment server 20 the updated, anonymized patient data record 32 together with the previous anonymized patient data record 32 belonging to the same patient. In at least one further method step 114, the patient recruitment server 20 receives by means of the data receiving module 76 the updated, anonymized patient data record 32 together with the previous anonymized patient data record 32 belonging to the same patient. In at least one further method step 116, the data-record comparison module 40 compares the received anonymized patient data record 32 with the anonymized patient data record 32 stored in the patient recruitment database 42. In at least one further method step 118, the data-record comparison module 40 overwrites a matching anonymized patient data record 32 with the updated, anonymized patient data record 32.

FIG. 4 shows a flow diagram of method steps proceeding at least partially within the method step 90. In at least one method step 120, the patient recruitment module 48 of the database environment 10 requests from the patient recruitment server 20 by means of the outbound connection 28 at least one anonymized patient data record 32, with which the patient recruitment module 22 of the patient recruitment server 20 has associated at least one recruitment feature 72 at least in the method step 94. In at least one further method step 122, the patient recruitment module 48 of the database environment 10 receives a requested anonymized patient data record 32, with which a recruitment feature 72 has been associated. In at least one further method step 124, the identifier module 34 calculates an anonymized identifier on the basis of the received anonymized patient data record 32. In at least one further method step 126, the anonymized identifiers stored in the table 62 are decrypted. In at least one further method step 128, the, in particular decrypted, anonymized identifiers stored in the table 62 are compared with the identifier calculated in method step 124. In at least one further method step 130, associated patient data records 14 are determined from the table 62 by means of matching anonymized identifiers. In at least one further method step 132, the patient data records 14 determined in method step 130 are transmitted to the display module 54 for visual display. In at least one further method step 134, the display module 54 displays the unanonymized patient data records 14 that are consistent with the recruitment features 72 of a clinical study.

REFERENCE SIGNS 10 database environment
12 database module
14 patient data record
16 course of treatment
18 patient database
20 patient recruitment server
22 patient recruitment module
24 data transport unit
26 restriction module
28 outbound connection
30 anonymization module
32 anonymized patient data record
34 identifier module
36 assignment module
38 encryption module
40 data-record comparison module
42 patient recruitment database
44 Internet port
46 reverse identification module
48 patient recruitment module
50 patient-recruitment-server end
52 database-environment end
54 display module
56 transmitter
58 receiver
60 anonymized patient database
62 table
64 database server
66 restriction module
68 Cloud
70 recruitment feature database
72 recruitment feature
74 outbound connection
76 data receiving module
78 reverse identification unit
80 candidate list
82 method step
84 method step
86 method step
88 method step
90 method step
92 method step
94 method step
96 method step
98 method step
100 method step
102 method step
104 method step
106 method step
108 method step
110 method step
112 method step
114 method step
116 method step
118 method step
120 method step
122 method step
124 method step
126 method step
128 method step
130 method step
132 method step
134 method step

The invention claimed is:

1. A patient recruitment system, in particular for clinical studies,
having at least one database environment arranged in a specially secured access-restricted region of an intranet of a hospital information system, the at least one database environment
comprising at least one database module that is configured at least to store in a patient database at least patient data records containing at least one course of treatment of at least one patient,
comprising an anonymization module, which is configured to convert patient data records into anonymized patient data records, such that the patient data records anonymized by the anonymization module are free of identifiers and/or identifying features that are unambiguously attributable to a patient,
comprising an identifier module that calculates, on the basis of an anonymized patient data record, an unambiguous anonymized identifier, the unambiguous anonymized identifier being implemented as an unambiguous checksum, which is implemented to be temporally modifiable, such that the anonymized identifier changes when an anonymized patient data record changes, and
comprising an assignment module, which assigns the anonymized identifier to a patient data record from the patient database, the patient data record being associated with the anonymized patient data record,
having at least one patient recruitment server arranged in logistic separation from the database environment, the at least one patient recruitment server
comprising at least one patient recruitment module that is configured to search anonymized patient data records containing courses of treatment and compare the courses of treatment with at least one recruitment feature, and
having a data transport unit for a data transfer of at least the anonymized patient data records between the database environment and the patient recruitment server,
wherein the data transport unit comprises a restriction module, operating as a firewall, which restricts the data transfer to outbound connections originating from the database environment such that the data transfer between the database environment and the patient recruitment server can be controlled solely from a database-environment end,
wherein the restriction module prevents an emission of the unambiguous anonymized identifiers implemented as unambiguous checksums, and the unambiguous anonymized identifiers generated by the identifier module of the database environment, and implemented as unambiguous checksums, remain in the database environment permanently,
wherein, when an anonymized patient data record is updated that already exists in an anonymized patient database of the database module and is already provided with an anonymized identifier, the identifier module assigns to the associated updated anonymized patient data record an unambiguous updated anonymized identifier calculated on the basis of the associated updated anonymized patient data record, which is different from the anonymized identifier of the anonymized patient data record already existing in the anonymized patient database of the database module, wherein in a transmission of an updated anonymized patient data record from the database environment to the patient recruitment server, the data transport unit jointly transmits an original anonymized patient data record, wherein the patient recruitment server comprises a data-record comparison module, which on receipt of an already existing anonymized patient data record detects a congruency of the anonymized patient data records and causes the existing anonymized patient data record to be overwritten with the jointly received updated anonymized patient data record in a patient recruitment database of the patient recruitment server, wherein the patient recruitment server comprises a further identifier module, which is configured to assign anonymized identifiers, which are used to find the congruency of identical anonymized patient data records, to anonymized patient data records received from the data transport unit, and wherein a database entry of the patient recruitment database comprises at least one updated anonymized patient data record and at least one anonymized identifier calculated by the identifier module of the patient recruitment server.

2. The patient recruitment system as claimed in claim 1, comprising an encryption module of the database environment, which encrypts at least the anonymized identifiers associated with at least one anonymized patient data record.

3. The patient recruitment system as claimed in claim 1, wherein the identifier module uses for calculating the anonymized identifier at least one time, at least one medical diagnosis, at least one dosage, at least one laboratory value, and/or at least one medication.

4. The patient recruitment system as claimed in claim 1, wherein the patient recruitment server comprises at least one Internet port at least for receiving at least one recruitment feature.

5. The patient recruitment system as claimed in claim 1, wherein a patient recruitment module of the database environment requests from the patient recruitment server, by means of the outbound connection of the data transport unit, at least one anonymized patient data record, which has been assigned at least one recruitment feature by the patient recruitment module of the patient recruitment server.

6. The patient recruitment system as claimed in claim 5, wherein, on receipt of an anonymized patient data record requested by the patient recruitment module of the database environment, a reverse identification module of the database environment performs a reverse identification of the anonymized patient data record.

7. A method for recruiting patients for clinical studies by means of a patient recruitment system having at least one database environment arranged in a specially secured and access-restricted region of an intranet of a hospital information system, the at least one database environment comprising at least one database module that is configured to store in a patient database at least patient data records containing at least one course of treatment of at least one patient, comprising an anonymization module, which is configured to convert patient data records into anonymized patient data records, such that the patient data records anonymized by the anonymization module are free of identifiers and/or identifying features which can be unambiguously attributed to a patient, comprising an identifier module that calculates, on the basis of an anonymized patient data record, an unambiguous anonymized identifier, the unambiguous anonymized identifier being implemented as an unambiguous checksum, which is implemented to be temporally modifiable, such that the anonymized identifier changes when an anonymized patient data record changes, and comprising an assignment module, which assigns the anonymized identifier to a patient data record from the patient database which is associated with the anonymized patient data record, having at least one patient recruitment server arranged in logistic separation from the database environment, the at least one patient recruitment server comprising at least one patient recruitment module that is configured to search anonymized patient data records containing courses of treatment and compare the courses of treatment with at least one recruitment feature, and having a data transport unit for a data transfer of at least the anonymized patient data records between the database environment and the patient recruitment server, wherein the data transfer is restricted, by a restriction module of the data transport unit, the restriction module operating as a firewall, to outbound connections originating from the database environment in such a way that the data transfer between the database environment and the patient recruitment server can be controlled solely from a database-environment end, wherein an emission of the unambiguous anonymized identifiers implemented as unambiguous checksums is prevented by the restriction module, and the unambiguous anonymized identifiers generated by the identifier module of the database environment, and implemented as unambiguous checksums, remain in the database environment permanently, wherein, when an anonymized patient data record is updated that already exists in an anonymized patient database of the database module, and is already provided with an anonymized identifier, the identifier module assigns to the associated updated anonymized patient data record an unambiguous updated anonymized identifier calculated on the basis of the associated updated anonymized patient data record, which is different from the anonymized identifier of the anonymized patient data record already existing in the anonymized patient database of the database module before the update, wherein in a transmission of an updated anonymized patient data record from the database environment to the patient recruitment server, the data transport unit jointly transmits an original anonymized patient data record, wherein the patient recruitment server comprises a data-record comparison module, which on receipt of an already existing anonymized patient data record detects a congruency of the anonymized patient data records and causes the existing anonymized patient data record to be overwritten with the jointly received updated anonymized patient data record in a patient recruitment database of the patient recruitment server, wherein the patient recruitment server comprises a further identifier module, which assigns anonymized identifiers, which are used to find the congruency of identical anonymized patient data records, to anonymized patient data records received from the data transport unit, and wherein a database entry of the patient recruitment database comprises at least one updated anonymized patient data record and at least one anonymized identifier calculated by the identifier module of the patient recruitment server.

* * * * *